United States Patent [19]

Breslow et al.

[11] 3,996,347

[45] Dec. 7, 1976

[54] PLANT VIRUS TREATMENT

[75] Inventors: David Samuel Breslow; Arthur A. Chadwick, both of Wilmington, Del.

[73] Assignee: Hercules Incorporated, Wilmington, Del.

[22] Filed: Mar. 20, 1975

[21] Appl. No.: 561,395

[52] U.S. Cl. .............................................. 424/78
[51] Int. Cl.$^2$ ................ A61K 31/80; A61K 31/78; A61K 31/755
[58] Field of Search ..................................... 424/78

[56] References Cited

UNITED STATES PATENTS

| | | | |
|---|---|---|---|
| 3,624,218 | 11/1971 | Regelson | 424/78 |
| 3,749,771 | 7/1973 | Regelson | 424/78 |
| 3,773,923 | 11/1973 | Regelson | 424/78 |

*Primary Examiner*—Sam Rosen
*Attorney, Agent, or Firm*—Marion C. Staves

[57] ABSTRACT

It has been found that plant viruses and viroids can be inhibited by treating plants infected with or exposed to viruses or viroids with a virus-inhibiting amount of a maleic acid, maleic anhydride or fumaric acid copolymer.

17 Claims, No Drawings

PLANT VIRUS TREATMENT

This invention relates to a method of suppressing virus growth or infection in plants. More specifically, this invention relates to a method of preventing, inhibiting or retarding the infection by and multiplication of virsues in plants by foliar treatment with certain maleic acid, maleic anhydride or fumaric acid copolymers. It will be understood that the term "virus" as used herein is meant to include viroid.

The harmful effects of viruses on various plants have been recognized and chronicled for nearly a hundred years. All kinds of plants, both ornamental and economic, including annuals, biennials, perennials and trees become infected viruses. In some cases the harmful effects are severe and cause great loss. For example, agricultural statistics for the year 1972 estimate a 9.5% annual crop loss of sugar beets caused by virus infection. The loss of sugar cane for the same year was estimated at 14.5% and of tomatoes 6.0%.

Although the losses due to virus infection are impressive, few really effective chemical control measures have been developed. In the past, soil fumigation, heat treatment and the destruction of infected plants were about the only measures available.

It is an object of this invention to provide a method of treating plants with certain maleic acid, maleic anhydride or fumaric acid copolymers to suppress virus growth in the plants.

It is another object of this invention to protect plants exposed to viruses by treating the plants with the copolymers.

It is another object of this invention to provide a method of systemically treating plants to prevent or inhibit the growth of viruses in the plants.

These and other objects of the invention will become apparent from the detailed description of the invention below.

It has now been discovered that certain specific maleic acid, maleic anhydride or fumaric acid copolymers; their half-amide--half-acids or half-amide-half-nophytotoxic salts; their partially or completely hydrolyzed esters; and their nonphytotoxic salts are effective in suppressing plant viruses. The specific copolymers useful in the process of this invention are the copolymers of maleic acid, maleic anhydride or fumaric acid with a monomer selected from (1) divinyl ether; (2) allyl esters of monocarboxylic aliphatic acids containing 1 to 17 carbon atoms in the aliphatic chain; and (3) olefins having the formula

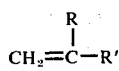

where R is a radical selected from hydrogen, $C_{1-18}$ alkyl, aryl containing 1 to 2 rings, alkyl substituted aryl containing 1 to 2 rings and 1 to 12 carbon atoms in the alkyl group, $C_{3-12}$ cycloalkyl, and the chloro, bromo and fluoro substituted counterparts of the above radicals; R' is a radical selected from $C_{1-18}$ alkyl, aryl containing 1 to 2 rings, alkyl substituted aryl containing 1 to 2 rings and 1 to 12 carbon atoms in the alkyl group, $C_{3-12}$ cycloalkyl, and the chloro, bromo and fluoro substituted counterparts of the above radicals; and R + R' contain no more than 18 carbon atoms; their half-amide--half-acids or half-amide--half-nonphytotoxic salts; their partially or completely hydrolyzed esters; and their nonphytotoxic salts, most preferably selected from the sodium, potassium, lithium and ammonium salts. Typical maleic acid, maleic anhydride and fumaric acid copolymers which are useful in this invention are divinyl ether--maleic anhydride copolymer, the half-amide of divinyl ether--maleic anhydride copolymer, partially hydrolyzed divinyl ether--diethyl fumarate copolymer, allyl acetate--maleic anhydride copolymer, allyl propionate--maleic anhydride copolymer, allyl butyrate--maleic anhydride copolymer, allyl isobutyrate--maleic anhydride copolymer, allyl pivalate--maleic anhydride copolymer, allyl hexanoate--maleic anhydride copolymer, allyl 2-ethylhexanoate--maleic anhydride copolymer, allyl laurate--maleic anhydride copolymer, allyl palmitate--maleic anhydride copolymer, allylstearate--maleic anhydride copolymer, the sodium salt of allyl propionate--maleic anhydride copolymer, the half-amide of allyl acetate--fumaric acid copolymer, styrene--maleic anhydride copolymer, hydrolyzed vinyltoluene--dimethyl maleate copolymer, 4-tert-butylstyrene--maleic anhydride copolymer, hydrolyzed 2,4,6-trimethylstyrene--dibutyl fumarate copolymer, the sodium salt of ethyl acid fumarate--styrene copolymer, 2,3,5,6-tetramethylstyrene--maleic anhydride copolymer, partially hydrolyzed chlorostyrene--dimethyl fumarate copolymer, hydrolyzed dimethyl fumarate--isobutylene copolymer, α-methylstyrene--maleic anhydride copolymer, α,p-dimethylstryrene--maleic anhydride copolymer, propylene--maleic anhydride copolymer, isobutylene--maleic anhydride copolymer, diisobutylene--maleic anhydride copolymer, hydrolyzed p-bromostyrene--bis(2-ethylhexylfumarate) copolymer, partially hydrolyzed m-fluorostyrene--diethyl maleate copolymer, p-(2,4,4-trimethyl-2-pentyl)styrene--maleic anhydride copolymer, the potassium salt of 1-octadecene--maleic acid copolymer, 2-vinylnaphthalene--maleic anhydride copolymer, vinylcyclobutane--maleic anhydride copolymer, vinylcyclopentane--maleic anhydride copolymer, hydrolyzed vinylcycloheptane--dimethyl fumarate copolymer, vinylcyclohexane--maleic anhydride copolymer, the half-amide half-sodium salt of vinylcyclooctane--maleic acid copolymer, vinylcyclononane--maleic anhydride copolymer, vinylcyclodecane--maleic anhydride copolymer, isopropenylcyclohexane--maleic anhydride copolymer, mixed α-olefins (containing 6–9 carbon atoms)--maleic anhydride copolymer, and the like.

While all of the above copolymers act to suppress plant viruses, those having a number average molecular weight of from about 1,000 to about 500,000 are preferred and from about 1,000 to about 100,000 most preferred.

In actual use the copolymer can be applied directly to the foliage but will generally be diluted with an inert liquid or solid carrier. For example, aqueous solutions, dispersions and emulsions can be used, as well as wettable powders and dusts where the copolymer is either mixed with a solid diluent or carried on a solid carrier. The particular concentration of copolymer in the carrier will depend on the particular copolymer used, the plant being treated and the virus being inhibited. However, the concentration used must be at least about 500 p.p.m. to about 15%, preferably at least about 4,500 p.p.m. to about 10% based on the weight of carrier.

The copolymer can be applied to the plant's foliage in a number of different ways such as by spraying the plant with a water solution, suspension or emulsion of the copolymer, in at least a sufficient concentration to inhibit virus growth in the plant. Other methods of application are dipping, in the case of potted plants, dusting with a dispersion of the copolymer in an inert powder, suspending small particles of the copolymer in a stream of air or other gas and spraying the plant with this suspension, or even sprinkling the copolymer on the plants in undiluted or powder form. Although these copolymers are effective at low concentrations, as stated above, higher concentrations can be used with the concentration being maintained below the level which will cause substantial phytotoxic injury to the plants.

When to apply the virus inhibiting compositions of this invention to any specific group of plants will be readily apparent to those skilled in the art. For example, tomato plants are apt to become infected when handled, such as during transplanting. Therefore, tomato plants should be protected by treatment before transplanting or immediately thereafter. In many cases a virus is spread by an insect vector and valuable plants vulnerable to attack by the insect and infection with the virus should be protected during the period of the insect's greatest activity. Plants treated with a copolymer in accordance with this invention can be protected and will resist virus infection for periods of up to a week or longer.

Since many of the copolymers are soluble in water after hydrolysis no dispersant will be necessary, although a wetting agent may still be desirable for maximum effectiveness. If the copolymer is not very soluble in water, an emulsifying agent may be required to keep it dispersed. Typical emulsifying agents which can be used are listed in the U.S. Department of Agricultrure Bulletin No. E607. The copolymers can also be applied dissolved or dispersed in organic solvents provided the solvents themselves are substantially nonphytotoxic to the plants. The organic solvent solutions of the copolymers can also themselves be emulsified with water. As indicated above, the copolymer can be admixed with an inert carrier such as talc, bentonite, kieselguhr, precipitated silica, diatomaceous earth, etc.

The process of this invention can be used to inhibit any plant virus, i.e., insect or nematode transmitted viruses and those mechanically transmitted through handling, cutting, grafting, etc. In the specification and claims describing and claiming this invention the plant viruses will be grouped according to type into sixteen groups as shown on pages 644 through 648 of Matthews Standard Text, Plant Virology, published by Academic Press Incorporated, New York, New York 1970. The type of plant virus included in each group is represented by one typical virus called the "type member". The type member of Group 1 is tobacco rattle virus and another member of the group is pea early-browning virus. The type member of Group 2 is tobacco mosaic virus and other members of the group are cucumber green mottle mosaic virus, odontoglossum ringspot virus, ribgrass mosaic virus, Sammon's Opuntia virus, sann hemp mosaic virus, tomato mosaic virus, etc. The type member of Group 3 is potato virus X and other members of the group are cactus virus X, clover yellow mosaic virus, hydrangea ringspot virus, white clover mosaic virus, etc. The type member of Group 4 is carnation latent virus and other members of the group are cactus virus 2, chrysanthemum virus B, passiflora latent virus, pea streak virus, potato virus M, potato virus S, red clover vein mosaic virus, etc. The type member of Group 5 is potato virus Y and other members of the group are bean common mosaic virus, bean yellow mosaic virus, beet mosaic virus, clover yellow vein virus, cowpea aphid-borne mosaic virus, Columbian datura virus, henbane mosaic virus, pea mosaic virus, potato virus A, soybean mosaic virus, sugar beet yellows viruses, sugar cane mosaic virus, tobacco etch virus, watermelon mosaic virus (South African), etc. The type member of Group 6 is alfalfa mosaic virus. The type member of Group 7 is pea enation mosaic virus. The type member of Group 8 is cucumber mosaic virus (S isolate) and other members of the group are tomato aspermy virus, yellow cucumber mosaic virus, etc. The type member of Group 9 is turnip yellow mosaic virus and other members of the group are cacao yellow mosaic virus, wild cucumber mosaid virus, Andean potato latent virus, belladonna mottle virus, dulcamara mottle virus, eggplant mosaic virus, ononis yellow mosaic virus, etc. The type member of Group 10 is cowpea mosaic virus (SB isolate) and other members of the group are bean pod mottle virus, broad bean strain virus, radish mosaic virus, red clover mottle virus, squash mosaic virus, true broad bean mosaic virus, etc. The type member of Group 11 is tobacco ringspot virus and other members of the group are arabis mosaic virus, grapevine fanleaf virus, raspberry ringspot virus, strawberry latent ringspot virus, tomato black ring virus, tomato ringspot virus, etc. The type member of Group 12 is tobacco necrosis virsu (A strain) and another member of the group is tobacco necrosis virus Strain D. The type member of Group 13 is brome mosaic virus and other members of the group are broad bean mottle virus, cowpea chlorotic mottle virus, etc. The type member of Group 14 is tomato bushy stunt virus and other members of the group are artichoke mottle crinkel virus, carnation Italian ringspot virus, pelargonium leaf curl virus, petunia asteroid mosaic virus, etc. The type member of Group 15 is tomato spotted wilt virus. The type member of Group 16 is cauliflower mosaic virus (cabbage B isolate) and another member of the group is dahlia mosaic virus. In addition to the above viruses the process of this invention can be used to inhibit any plant viroid such as chrysanthemum chlorotic mottle viroid, potato spindle tuber viroid, chyrsanthemum stunt viroid, citrus exocortis viroid, etc.

The following examples are presented to illustrate the process of this invention. Parts and percentages are by weight unless otherwise stated.

EXAMPLES 1-5

To determine the effect of certain copolymers on plant virus infection, local lesion assays are performed using tobacco ringspot virus (TRSV). Assays are done on nine to fourteen day old cowpea (*Vigna sinensis*) seedlings selected for uniformity of size. In each case solutions of 10,000 p.p.m. of the copolymer in water, adjusted to pH 7, are sprayed on the primary leaves to "run-off". The plants are not watered until after inoculation with TRSV.

Inoculum is prepared by grinding TRSV-infected cucumber tissue in a mortar and pestle at a 1:4 weight per volume with 0.05 phosphate buffer at a pH of 7.0 to 7.2. Twenty-four hours after spraying with the copolymer the primary leaves are dusted with 600 mesh carborundum and inoculated. The inoculum is applied with a 2.5 cm. brush using one stroke per half leaf. Approximately 10 minutes after inoculation with the virus the leaves are rinsed with tap water. Control plants are treated exactly the same way except they are not treated with a copolymer. Lesions are counted approximately 3 to 6 days after inoculation. An average is taken from groups of control plants and treated plants and the results reported as percent reduction in lesions. The specific copolymer and the percent reduction in lesions is tabulated below in Table I Table I

| Examples | Copolymer | % Reduction |
|---|---|---|
| 1 | Divinyl ether—maleic anhydride copolymer[1] | 97 |
| 2 | Divinyl ether—maleic anhydride copolymer[2] | 84 |
| 3 | alpha-Olefin—maleic anhydride copolymer[3] | 78 |
| 4 | Styrene—maleic anhydride copolymer[4] | 98 |
| 5 | Diisobutylene—maleic anhydride copolymer[5] | 99 |

Footnotes
[1]Prepared from divinyl ether and maleic anhydride in a mole ratio of 1:2 and having a number average molecular weight of 1,900.
[2]Prepared from divinyl ether and maleic anhydride in a mole ratio of 1:2 and having a number average molecular weight of 17,000.
[3]Prepared from a mixture of $C_{8-9}$ alpha-olefins and maleic anhydride in a mole ratio of approximately 1:1 having a drop softening point of 180° C.
[4]Commercial product prepared from styrene and maleic anhydride in a mole ratio of 1:1 and sold under the tradename SMA resin 1000A by Arco Chemical Co., Division of Atlantic Richfield Co.
[5]The commercial copolymer sold under the tradename Tamol 731 by Rohm & Haas Company.

EXAMPLES 6–8

These examples illustrate the effect of various copolymers on the growth of alfalfa mosaic virus.

Assays are conducted on cowpeas using inoculum prepared from infected cucumber tissue exactly as described in EXAMPLES 1–5. The specific copolymers used and the percentage reduction in lesions is tabulated below in Table II.

Table II

| Examples | Copolymer | % Reduction |
|---|---|---|
| 6 | Divinyl ether—maleic anhydride copolymer[6] | 90 |
| 7 | Styrene—maleic anhydride copolymer[7] | 98 |
| 8 | Diisobutylene—maleic anhydride copolymer[8] | 97 |

Footnotes
[6]As described in Example 1.
[7]As described in Example 4.
[8]As described in Example 5.

EXAMPLES 9 and 10

These examples illustrate the effect of various copolymers on the growth of tobacco mosaic virus.

Assays are conducted exactly as described in Examples 1–5 except that they are done on pinto bean (*Phaseolus vulgaris*) seedlings using inoculum prepared from tobacco mosaic virus-infected tobacco tissue. The specific copolymer used and the percent reduction in lesions is tabulated below in Table III.

Table III

| Examples | Copolymer | % Reduction |
|---|---|---|
| 9 | Divinyl ether—maleic anhydride copolymer[9] | 90 |

Table III-continued

| Examples | Copolymer | % Reduction |
|---|---|---|
| 10 | Styrene—maleic anhydride copolymer[10] | 97 |

Footnotes
[9]As described in Example 1.
[10]As described in Example 4.

EXAMPLES 11–13

These examples illustrate the effect of various copolymers on the growth of tomato ringspot virus. Assays are conducted on cowpeas using inoculum prepared from infected cucumber tissue exactly as described in Examples 1–5. The specific copolymers used and the percent reduction in lesions is tabulated below in Table IV.

Table IV

| Examples | Copolymer | % Reduction |
|---|---|---|
| 11 | Divinyl ether—maleic anhydride copolymer[11] | 88 |
| 12 | Styrene—maleic anhydride copolymer[12] | 67 |
| 13 | Diisobutylene—maleic anhydride copolymer[13] | 90 |

Footnotes
[11]As described in Example 1.
[12]As described in Example 4.
[13]As described in Example 5.

EXAMPLES 14–19

These examples illustrate the effect of various concentrations of the divinyl ether–maleic anhydride copolymer described in Example 1 on the growth of tobacco mosaic virus.

Assays are conducted exactly as described in Examples 9 and 10 except that in each example groups of pinto bean seedlings are treated with a different concentration of aqueous divinyl ether–maleic anhydride copolymer solution. The specific concentration used and the percent reduction in lesions is tabulated below in Table V.

Table V

| Examples | Concentration | % Reduction |
|---|---|---|
| 14 | 500 p.p.m. | 27.5 |
| 15 | 1000 p.p.m. | 25.0 |
| 16 | 2500 p.p.m. | 31.0 |
| 17 | 5000 p.p.m. | 62.0 |
| 18 | 10000 p.p.m. | 79.0 |
| 19 | 5 % | >85.0 |

EXAMPLES 20–22

These examples illustrate the effect of post-treating a plant infected with a virus.

Assays are conducted exactly the same as described in Examples 1–5 except the cowpea seedlings are first inoculated with tobacco ringspot virus and then later sprayed with a 10,000 p.p.m. aqueous solution of the divinyl ether–maleic anhydride copolymer described in Example 1. The number of hours after inoculation that the seedlings are sprayed and the percent reduction in lesions is tabulated below in Table VI.

Table VI

| Examples | Hours after Inoculation | % Reaction |
|---|---|---|
| 20 | 2 | 59 |
| 21 | 6 | 50 |
| 22 | 12 | 52 |

EXAMPLE 23

This example illustrates the systemic action of the copolymers on the growth of plant viruses.

Assays are conducted as described in Examples 1–5 except the primary leaves of the cowpea seedlings are treated on the underside with a 10,000 p.p.m. aqueous solution of the divinyl ether--maleic anhydride copolymer described in Example 1 and then 24 hours later inoculated with tobacco ringspot virus on the upper surface of the leaves. There is a 38% reduction in the number of lesions on the treated seedlings as opposed to the untreated controls.

EXAMPLE 24

This example illustrates the systemic action of the copolymers on the growth of plant viruses.

Assays are conducted as described in Examples 1–5 except that only one of the primary leaves of the cowpea is treated with a 10,000 p.p.m. aqueous solution of the divinyl ether--maleic anhydride copolymer described in Example 1 and then 24 hours later the opposite primary leaf is inoculated with tobacco ringspot virus. There is approximately a 20% reduction in the number of lesions on the treated seedlings as opposed to the untreated controls.

EXAMPLE 25

This example illustrates the systemic action of the copolymers on the growth of plant virus.

Assays are conducted as described in Examples 1–5 except only the distal half of the upper surface of the primary leaves of the cowpeas are treated with a 10,000 p.p.m. aqueous solution of the divinyl ether---maleic anhydride copolymer described in Example 1 and then 24 hours later the whole upper surface of the primary leaves are inoculated with tobacco ringspot virus. There is a 40% reduction in the number of lesions on the treated seedlings as opposed to the untreated controls.

EXAMPLE 26

This example illustrates the inhibition of the growth of a plant viroid by treating with a copolymer.

Chyrsanthemum (variety deep ridge) rooted cuttings are sprayed to run-off with an aqueous solution of 10,000 p.p.m. of the divinyl ether--maleic anhydride copolymer described in Example 1. Inoculum is prepared by grinding chyrsanthemum chlorotic mottle viroid-infected chrysanthemum tissue in a mortar and pestle at 1:4 weight per volume with 0.05 M phosphate buffer at a pH of 7.0 to 7.2. Twenty-four hours after spraying with the polymer, three leaves on each rooted cutting are dusted with 600 mesh carborundum and inoculated. The inoculum is applied with a 2.5 cm. brush using one stroke per half leaf. Approximately 10 minutes after inoculation with the viroid the leaves are rinsed with tap water. Control plants are treated exactly the same way except they are not treated with the copolymer. Within 15 days to about 3 weeks the control plants develop a yellow mottle and growth of the plants is stunted. The treated plants on the other hand, are essentially free of yellow mottle and unstunted.

EXAMPLES 27–39

These examples illustrate the treatment of various plant viruses with a maleic anhydride coplymer.

Assays are conducted on young seedlings, selected for their suitability as local lesion hosts. In each case an aqueous solution of 10,000 p.p.m. of divinyl ether--maleic anhydride copolymer described in Example 1 is sprayed on the leaves to "run-off". Inoculum is prepared by grinding virus-infected tissue from a suitable propagation species in a mortar and pestle at a 1:4 weight per volume with 0.05 M phosphate buffer at a pH of 7.0 to 7.2. Twenty-four hours after spraying with the divinyl ether--maleic anhydride copolymer the primary leaves are dusted with 600 mesh carborundum and inoculated. The inoculum is applied with a 2.5 cm. brush using one stroke per half leaf. Approximately 10 minutes after inoculation with the virus the leavves are rinsed with tap water. Control plants are treated exactly the same way except they are not treated with the divinyl ether--maleic anhydride copolymer. After a period of approximately 3 to 9 days the treated seedlings are compared with the untreated controls. In each case a marked decrease in the growth of the plant virus as evidenced by local lesions or mottle was noted in those plants which had been treated with the divinyl ether--maleic anhydride copolymer. The specific virus, the propagation species used to maintain the culture and from which the inoculum is prepared, and the local lesion host on which the assays are conducted are tabulated below in Table VII.

Table VII

| Example | Virus | Propagation Species | Local Lesion Hosts |
|---|---|---|---|
| 27 | Tobacco rattle virus | Tobacco (Nicotiana clevelandii) | Chenopodium amaranticolor |
| 28 | Potato virus X | Tobacco (Nicotiana tabacum) | Globe amaranth (Gomphrena globosa) |
| 29 | Carnation latent virus | Carnation (Dianthus barbatus) | Chenopodium amaranticolor |
| 30 | Potato virus Y | Tobacco (Nicotiana glutinosa) | Chenopodium quinoa |
| 31 | Pea enation mosaic virus | Garden peas (Pisum sativum) | Chenopodium amaranticolor |
| 32 | Cucumber mosaic virus | Tobacco (Nicotiana glutinosa) | Cowpea (Vigna sinensis) |
| 33 | Turnip yellow mosaic virus | Chinese cabbage (Brassica pekinensis) | Chinese cabbage (Brassica pekinensis) |
| 34 | Cowpea mosaic virus (SB Isolate) | Cowpea (Vigna sinensis) | Pinto bean (Phaseolus vulgaris) |
| 35 | Tobacco necrosis virus (A strain) | Tobacco (Nicotiana tabacum) | Pinto bean (Phaseolus vulgaris) |
| 36 | Brome mosaic virus | Barley (Hordeum vulgare) | Chenopodium hybridum |
| 37 | Tomato bushy stunt virus | Tobacco (Nicotiana clevelandii) | Chenopodium amaranticolor |

Table VII-continued

| Example | Virus | Propagation Species | Local Lesion Hosts |
| --- | --- | --- | --- |
| 38 | Tomato spotted wilt virus | Tobacco (Nicotiana rustica) | Petunia hybrida (v. pink beauty) |
| 39 | Cauliflower mosaic virus | Tendergreen mustard (Brassica campestris) | Tendergreen mustard (Brassica campestris |

What we claim and desire to protect by Letters Patent is:

1. A process of suppressing plant virus growth in plants which comprises applying to the foliage of said plants a plant virus inhibiting amount of at least one agent selected from the copolymers of maleic acid, maleic anhydride or fumaric acid with a monomer selected from 1) divinyl ether; 2) allyl esters of monocarboxylic aliphatic acids containing 1 to 17 carbon atoms in the aliphatic chain; and 3) olefins having the formula

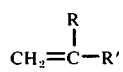

where R is a radical selected from hydrogen, $C_{1-18}$ alkyl, aryl containing 1 to 2 rings, alkyl substituted aryl containing 1 to 2 rings and 1 to 12 carbon atoms in the alkyl group, $C_{3-12}$ cycloalkyl, and the above defined R radicals substituted with chloro, bromo and fluoro substituents R' is a radical selected from $C_{1-18}$ alkyl, aryl containing 1 to 2 rings, alkyl substituted aryl containing 1 to 2 rings and 1 to 12 carbon atoms in the alkyl group, $C_{3-12}$ cycloalkyl, and the above defined R' radicals substituted with chloro, bromo and fluoro substituents; and R + R' contain no more than 18 carbon atoms; their half-amide--half-acids or half-amide--half-nonphytotoxic salts; their partially or completely hydrolyzed esters; and their nonphytotoxic salts.

2. The process of claim 1 wherein the agent is applied in the form of a liquid spray.

3. The process of claim 2 wherein the said liquid spray is an aqueous solution.

4. The process of claim 1 wherein the agent is applied in the form of a dust.

5. The process of claim 1 wherein the agent is applied in the form of a wettable powder.

6. The process of claim 1 wherein the virus is selected from the Group 3 viruses.

7. The process of claim 1 wherein the virus is selected from the Group 5 viruses.

8. The process of claim 1 wherein the virus is selected from the Group 8 viruses.

9. The process of claim 1 wherein the virus is selected from the Group 10 viruses.

10. The process of claim 1 wherein the virus is selected from the Group 11 viruses.

11. The process of claim 1 wherein the virus is sugar cane mosaic virus.

12. The process of claim 1 wherein the virus is sugar beet yellows viruses.

13. The process of claim 1 wherein the virus is tobacco ringspot virus.

14. The process of claim 1 wherein the agent is a copolymer of maleic anhydride.

15. The process of claim 14 wherein the copolymer of maleic anhydride is a styrene--maleic anhydride copolymer.

16. The process of claim 14 wherein the copolymer of maleic anhydride is a divinyl ether--maleic anhydride copolymer.

17. A process of protecting plants exposed to plant viruses which comprises applying to the foliage of said plants a plant virus inhibiting amount of at least one agent selected from the copolymers of maleic acid, maleic anhydride or fumaric acid with a monomer selected from 1) divinyl ether; 2) allyl esters of monocarboxylic aliphatic acids containing 1 to 17 carbon atoms in the aliphatic chain; and 3) olefins having the formula

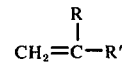

where R is a radical selected from hydrogen, $C_{1-18}$ alkyl, aryl containing 1 to 2 rings, alkyl substituted aryl containing 1 to 2 rings and 1 to 12 carbon atoms in the alkyl group, $C_{3-12}$ cycloalkyl, and the above defined R radicals substituted with chloro, bromo and fluoro substituents; R' is a radical selected from $C_{1-18}$ alkyl, aryl containing 1 to 2 rings alkyl substituted aryl containing 1 to 2 rings and 1 to 12 carbon atoms in the alkyl group, $C_{3-12}$ cycloalkyl, and the above defined R' radicals substituted with chloro, bromo and fluoro substituents; and R + R' contain no more than 18 carbon atoms; their half-amide--half-acids or half-amide--half-nonphytotoxic salts; their partially or completely hydrolyzed esters; and their nonphytotoxic salts.

* * * * *